US010568988B2

(12) United States Patent
Monteiro et al.

(10) Patent No.: US 10,568,988 B2
(45) Date of Patent: Feb. 25, 2020

(54) METHODS FOR LOCALIZED MODIFICATION OF TISSUE PRODUCTS

(71) Applicant: LifeCell Corporation, Branchburg, NJ (US)

(72) Inventors: Gary Monteiro, Grosse Pointe, MI (US); Christopher T. Wagner, Flemington, NJ (US); Neil L. Rodriguez, Clinton, NJ (US); Aubrey Irene Delossantos, Bridgewater, NJ (US)

(73) Assignee: LifeCell Corporation, Madison, NJ (US)

( * ) Notice: Subject to any disclaimer, the term of this patent is extended or adjusted under 35 U.S.C. 154(b) by 397 days.

(21) Appl. No.: 15/419,076

(22) Filed: Jan. 30, 2017

(65) Prior Publication Data

US 2017/0209619 A1     Jul. 27, 2017

Related U.S. Application Data

(62) Division of application No. 14/162,915, filed on Jan. 24, 2014, now Pat. No. 9,592,254.

(60) Provisional application No. 61/761,298, filed on Feb. 6, 2013.

(51) Int. Cl.
```
A61L 27/36      (2006.01)
A61K 35/12      (2015.01)
A61L 27/24      (2006.01)
```

(52) U.S. Cl.
CPC .......... *A61L 27/3687* (2013.01); *A61K 35/12* (2013.01); *A61L 27/24* (2013.01)

(58) Field of Classification Search
CPC ................................ A61L 27/36; A61K 35/12
See application file for complete search history.

(56) References Cited

U.S. PATENT DOCUMENTS

| | | |
|---|---|---|
| 4,582,640 A | 4/1986 | Smestad et al. |
| 4,902,508 A | 2/1990 | Badylak et al. |
| 4,969,912 A | 11/1990 | Kelman et al. |
| 5,104,957 A | 4/1992 | Kelman et al. |
| 5,131,850 A | 7/1992 | Brockbank |
| 5,160,313 A | 11/1992 | Carpenter et al. |
| 5,231,169 A | 7/1993 | Constantz et al. |
| 5,254,133 A | 10/1993 | Seid |
| 5,275,826 A | 1/1994 | Badylak et al. |
| 5,284,655 A | 2/1994 | Bogdansky et al. |
| 5,332,802 A | 7/1994 | Kelman et al. |
| 5,332,804 A | 7/1994 | Florkiewicz et al. |
| 5,336,616 A | 8/1994 | Livesey et al. |
| 5,364,756 A | 11/1994 | Livesey et al. |
| 5,489,304 A | 2/1996 | Orgill et al. |
| 5,547,681 A | 8/1996 | Clark et al. |
| 5,613,982 A | 3/1997 | Goldstein |
| 5,632,778 A | 5/1997 | Goldstein |
| 5,641,518 A | 6/1997 | Badylak et al. |
| 5,728,752 A | 3/1998 | Scopelianos et al. |
| 5,739,176 A | 4/1998 | Dunn et al. |
| 5,800,537 A | 9/1998 | Bell |
| 5,893,888 A | 4/1999 | Bell |
| 5,993,844 A | 11/1999 | Abraham et al. |
| 6,027,743 A | 2/2000 | Khouri et al. |
| 6,096,347 A | 8/2000 | Geddes et al. |
| 6,113,623 A | 9/2000 | Sgro |
| 6,166,288 A | 12/2000 | Diamond et al. |
| 6,179,872 B1 | 1/2001 | Bell et al. |
| 6,194,136 B1 | 2/2001 | Livesey et al. |
| 6,326,018 B1 | 12/2001 | Gertzman et al. |
| 6,371,992 B1 | 4/2002 | Tanagho et al. |
| 6,381,026 B1 | 4/2002 | Schiff et al. |
| 6,432,710 B1 | 8/2002 | Boss, Jr. et al. |
| 6,485,723 B1 | 11/2002 | Badylak et al. |
| 6,576,265 B1 | 6/2003 | Spievack |
| 6,666,892 B2 | 12/2003 | Hiles et al. |
| 6,835,385 B2 | 12/2004 | Buck |
| 6,933,326 B1 | 8/2005 | Griffey et al. |
| 7,358,284 B2 | 4/2008 | Griffey et al. |
| 7,425,322 B2 | 9/2008 | Cohn et al. |
| 7,498,040 B2 | 3/2009 | Masinaei et al. |
| 7,498,041 B2 | 3/2009 | Masinaei et al. |
| 7,799,767 B2 | 9/2010 | Lamberti et al. |
| 7,838,021 B2 | 11/2010 | Lafont et al. |
| 8,067,149 B2 | 11/2011 | Livesey et al. |
| 8,257,372 B2 * | 9/2012 | Swain .................... A61B 17/11 606/152 |
| 8,324,449 B2 | 12/2012 | McQuillan et al. |
| 9,206,442 B2 | 12/2015 | Chen |
| 9,238,793 B2 | 1/2016 | Chen et al. |
| 2002/0103542 A1 | 8/2002 | Bilbo |
| 2003/0035843 A1 | 2/2003 | Livesey et al. |
| 2003/0143207 A1 | 7/2003 | Livesey et al. |
| 2004/0037735 A1 | 2/2004 | DePaula et al. |
| 2004/0191226 A1 | 9/2004 | Badylak |
| 2005/0028228 A1 | 2/2005 | McQuillan et al. |
| 2005/0159822 A1 | 7/2005 | Griffey et al. |
| 2006/0073592 A1 | 4/2006 | Sun et al. |
| 2006/0127375 A1 | 6/2006 | Livesey et al. |
| 2006/0159641 A1 | 7/2006 | Girardot et al. |
| 2006/0210960 A1 | 9/2006 | Livesey et al. |
| 2006/0272102 A1 | 12/2006 | Liu et al. |

(Continued)

FOREIGN PATENT DOCUMENTS

| | | |
|---|---|---|
| CN | 1266716 A | 9/2000 |
| JP | 2004-107303 A | 4/2004 |

(Continued)

OTHER PUBLICATIONS

Stella et al. On the biomechanical function of scaffolds for engineering load bearing soft tissues, Acta Biomaterials, vol. 6, p. 2365-2381. (Year: 2010).*

(Continued)

Primary Examiner — Taeyoon Kim
Assistant Examiner — Tiffany M Gough
(74) Attorney, Agent, or Firm — McCarter & English, LLP; Matthew R. Van Eman

(57) ABSTRACT

Methods for treating tissue matrices and tissue matrices produced according to the methods are provided. The methods can include treating select portions of a tissue matrix with a cross-linking agent and/or a proteolytic enzyme to produce a tissue matrix with variable mechanical and/or biological properties.

9 Claims, 8 Drawing Sheets

(56) References Cited

U.S. PATENT DOCUMENTS

| | | | |
|---|---|---|---|
| 2007/0009586 | A1 | 1/2007 | Cohen et al. |
| 2007/0078522 | A2 | 4/2007 | Griffey et al. |
| 2007/0104759 | A1 | 5/2007 | Dunn et al. |
| 2007/0248575 | A1 | 10/2007 | Connor et al. |
| 2008/0027542 | A1 | 1/2008 | McQuillan et al. |
| 2008/0027562 | A1 | 1/2008 | Fujisato et al. |
| 2009/0035289 | A1 | 2/2009 | Wagner et al. |
| 2009/0130221 | A1 | 5/2009 | Bolland et al. |
| 2009/0239809 | A1 | 9/2009 | Chen et al. |
| 2009/0306790 | A1 | 12/2009 | Sun |
| 2010/0021961 | A1 | 1/2010 | Fujisato et al. |
| 2010/0040687 | A1 | 2/2010 | Pedrozo et al. |
| 2010/0209408 | A1 | 8/2010 | Stephen A. et al. |
| 2010/0233235 | A1 | 9/2010 | Matheny et al. |
| 2010/0272782 | A1 | 10/2010 | Owens et al. |
| 2011/0020271 | A1 | 1/2011 | Niklason et al. |
| 2011/0021753 | A1 | 1/2011 | Huang |
| 2012/0010728 | A1 | 1/2012 | Sun et al. |
| 2012/0040013 | A1 | 2/2012 | Owens et al. |
| 2012/0252065 | A1 | 10/2012 | Rozenszain et al. |
| 2012/0263763 | A1 | 10/2012 | Sun et al. |
| 2012/0276213 | A1 | 11/2012 | Chen |
| 2013/0013068 | A1 | 1/2013 | Forsell et al. |
| 2013/0053960 | A1 | 2/2013 | Park et al. |
| 2013/0121970 | A1 | 5/2013 | Owens et al. |
| 2013/0158676 | A1 | 6/2013 | Hayzlett et al. |
| 2014/0004549 | A1 | 1/2014 | Chen et al. |
| 2014/0377833 | A1 | 12/2014 | Chen et al. |

FOREIGN PATENT DOCUMENTS

| | | |
|---|---|---|
| WO | 99/63051 A2 | 12/1999 |
| WO | 99/65470 A1 | 12/1999 |
| WO | 2001/091671 A1 | 12/2001 |
| WO | 2002/049687 A1 | 6/2002 |
| WO | 2003/017826 A2 | 3/2003 |
| WO | 2003/032735 A1 | 4/2003 |
| WO | 2004/020470 A1 | 3/2004 |
| WO | 2005/009134 A1 | 2/2005 |
| WO | 2007/043513 A1 | 4/2007 |
| WO | 2009/009620 A2 | 1/2009 |
| WO | 2010/019753 A2 | 2/2010 |
| WO | 2010/078353 A2 | 7/2010 |
| WO | 2012/142419 A1 | 10/2012 |
| WO | 2012/166784 A1 | 12/2012 |
| WO | 2013/016571 A1 | 1/2013 |

OTHER PUBLICATIONS

Ahn et al., "The past, present, and future of xenotransplantation" Yonsei Med J., 45(6):1017-1024 (Dec. 31, 2004).

Allman et al., "Xenogeneic Extracellular Matrix Grafts Elicit a TH2-Restricted Immune Response" Transplantation, 71(11):1631-1640 (Jun. 15, 2001).

Aycock et al., "Parastomal Hernia Repair With Acellular Dermal Matrix" J. Wound Ostomy Continence Nurs., 34(5):521-523 (2007).

Badylak et al., "Endothelial cell adherence to small intestinal submucosa: An acellular bioscaffold" Biomaterials, 20:2257-2263 (1999).

Badylak et al., "Extracellular Matrix as a Biological Scaffold Material: Structure and Function" Acta Biomaterialia, 5(1):1-13 (2009).

Beniker et al., "The use of acellular dermal matrix as a scaffold for periosteum replacement" Orthopedics, 26(5 Suppl):s591-s596 (May 2003).

Bruder et al., "The Effect of Implants Loaded with Autologous Mesenchymal Stem Cells on the Healing of Canine Segmental Bone Defects" J. Bone Joint Surg., 80:985-986 (1998).

Buma et al., "Tissue engineering of the meniscus" Biomaterials, 25(9):1523-1532 (2004).

Chaplin et al., "Use of an Acellular Dermal Allograft for Dural Replacement: An Experimental Study" Neurosurgery, 45(2):320-327 (Aug. 1999).

Chen et al. "Acellular Collagen Matrix as a Possible 'Off the Shelf' Biomaterial for Urethral Repair" Urology, 54(3):407-410 (1999).

Collins et al., "Cardiac xenografts between primate species provide evidence for the importance of the ?-galactosyl determinant in hyperacute rejection" J. Immunol., 154:5500-5510 (1995).

Costantino et al., "Human Dural Replacement With Acellular Dermis: Clinical Results and a Review of the Literature" Head & Neck, 22:765-771 (Dec. 2000).

Dobrin et al., "Elastase, collagenase, and the biaxial elastic properties of dog carotid artery" Am. J. Physiol. Heart Circ. Physiol., 247:H124-H131 (1984).

Edel, "The use of a connective tissue graft for closure over an immediate implant covered with occlusive membrane" Clin. Oral Implants Res., 6:60-65 (1995) (Abstract).

Fowler et al., "Ridge Preservation Utilizing an Acellular Dermal Allograft and Demineralized Freeze-Dried Bone Allograft: Part II. Immediate Endosseous Impact Placement" J. Periodontol., 71:1360-1364 (2000).

Fowler et al., "Root Coverage with an Acellular Dermal Allograft: A Three-Month Case Report" J. Contemp. Dental Pract., 1(3):1-8 (2000).

Galie, Peter A., and Jan P. Stegemann. "Simultaneous application of interstitial flow and cyclic mechanical strain to a three-dimensional cell-seeded hydrogel." Tissue Engineering Part C: Methods 17.5 (Feb. 2011): 527-536.

Galili et al., "Interaction Between Human Natural Anti-?-Galactosyl Immunoglobulin G and Bacteria of the Human Flora" Infect. Immun., 56(7):1730-1737 (1988).

Galili et al., "Interaction of the Natural Anti-Gal Antibody with ?-Galactosyl Epitopes: a Major Obstacle for Xenotransplantation in Humans" Immunology Today, 14(10):480-482 (1993).

Galili et al., "Man, Apes, and Old World Monkeys Differ from Other Mammals in the Expression of ?-Galactosyl Epitopes on Nucleated Cells" J. Biol. Chem., 263(33):17755-17762 (1988).

Gamba et al. "Experimental abdominal wall defect repaired with acellular matrix" Pediatr. Surg. Int., 18:327-331 (2002).

Gebhart et al., "A radiographical and biomechanical study of demineralized bone matrix implanted into a bone defect of rat femurs with and without bone marrow" Acta Orthop. Belg., 57(2):130-143 (1991) (Abstract).

Greenstein et al., "Parastomal Hernia Repair Using Cross-Linked Porcine Dermis: Report of a Case" Surg. Today, 38:1048-1051 (2008).

Griffey et al., "Particulate Dermal Matrix as an Injectable Soft Tissue Replacement Material" J. Biomed. Mater. Res. (Appl. Biomater.), 58(1):10-15 (2001).

Hamadeh et al., "Human natural anti-Gal IgG regulates alternative complement pathway activation on bacterial surfaces," J. Clin. Invest. 89:1223-1235 (1992).

Harris, "A Comparative Study of Root Coverage Obtained with an Acellular Dermal Matrix Versus a Connective Tissue Graft: Results of 107 Recession Defects in 50 Consecutively Treated Patients" Int. J. Periodontics Restorative Dentist., 20(1):51-59 (2000).

Harris, "Root Coverage With a Connective Tissue With Partial Thickness Double Pedicle Graft and an Acellular Dermal Matrix Graft: A Clinical and Histological Evaluation of a Case Report" J. Periodontol., 69:1305-1311 (1998).

International Search Report and Written Opinion, dated Jul. 16, 2014, for International Patent Application No. PCT/US2014/012854.

Ionescu et al., "Effect of Papain and Bromelin on Muscle and Collagen Proteins in Beef Meat," The Annals of the University Dunarea de Jos of Galati. Fascicle VI, Food Technology, New Series, pp. 9-16, 2008.

Karlinsky et al., "In Vitro Effects of Elastase and Collagenase on Mechanical Properties of Hamster Lungs," Chest, 69(2):275-276 (1976).

Kish et al., "Acellular Dermal Matrix (AlloDerm): New Material in the Repair of Stoma Site Hernias" The American Surgeon, 71:1047-1050 (Dec. 2005).

Kridel et al., "Septal Perforation Repair with Acellular Human Dermal Allograft" Arch. Otolaryngol. Head Neck Surg., 124:73-78 (Jan. 1998).

(56) References Cited

OTHER PUBLICATIONS

Laidlaw et al., "Tympanic Membrane Repair With a Dermal Allograft" Laryngoscope, 111:702-707 (Apr. 2001).
Lee et al., "In vitro evaluation of a poly(lactide-co-glycolide)-collagen composite scaffold for bone regeneration" Biomaterials, 27:3466-3472 (2006).
Lu et al., "Novel Porous Aortic Elastin and Collagen Scaffolds for Tissue Engineering" Biomaterials, 25(22):5227-5237 (2004).
Reihsner et al., "Biomechanical properties of elastase treated palmar aponeuroses," Connective Tissue Research, 26:77-86 (1991).
Simon et al., "Early failure of the tissue engineered porcine heart valve SYNERGRAFT™ in pediatric patients" Eur. J. Cardiothorac. Surg., 23(6):1002-1006 (2003).
Tedder et al., "Stabilized Collagen Scaffolds for Heart Valve Tissue Engineering," Tissue Engineering: Part A, pp. 1-12 (2008).
Xu, "A Porcine-Derived Acellular Dermal Scaffold that Supports Soft Tissue Regeneration: Removal of Terminal Galactose-?-(1,3)-Galactose and Retention of Matrix Structure," Tissue Engineering, vol. 15, 1-13 (2009).
Yuan et al., "Effects of collagenase and elastase on the mechanical properties of lung tissue strips," J. App. Physiol., 89:3-14 (2000).
Zheng et al. "Porcine small intestine submucosa (SIS) is not an acellular collagenous matrix and contains porcine DNA: Possible implications in human implantation" J. Biomed. Mater. Res. B: Appl. Biomater., 73(1):61-67 (2005).

\* cited by examiner

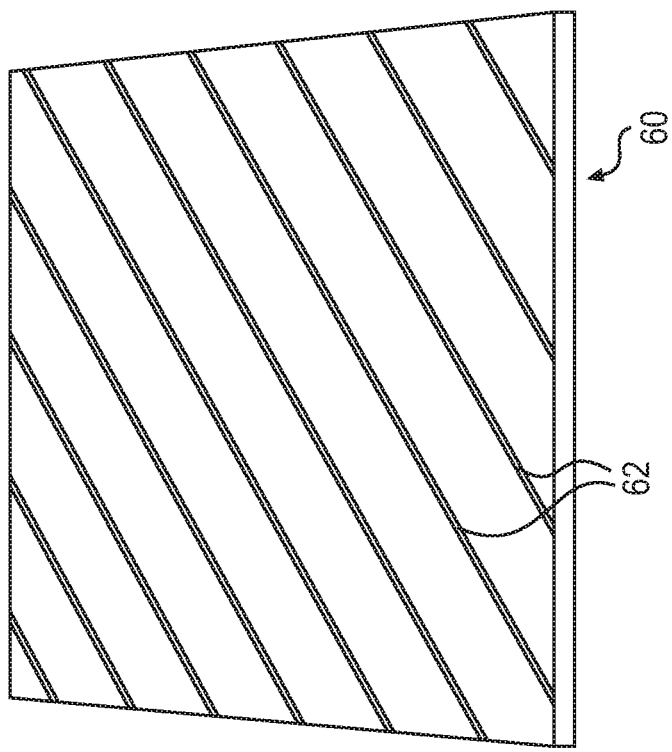
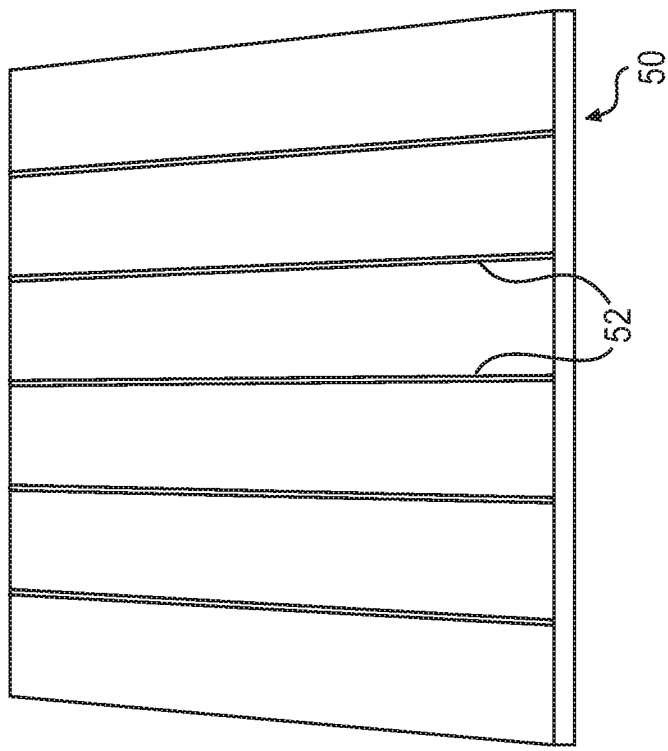

020
METHODS FOR LOCALIZED MODIFICATION OF TISSUE PRODUCTS

This application is a continuation of U.S. patent application Ser. No. 14/162,915, filed Jan. 24, 2014, which claims priority under 35 U.S.C. § 119 to U.S. Provisional Patent Application 61/761,298, which was filed on Feb. 6, 2013, each of the above applications being incorporated by reference in its entirety.

The present disclosure relates to tissue matrices, and more particularly, to methods for localized modification of mechanical and/or biological properties of tissue matrices.

Various tissue-derived products are used to regenerate, repair, or otherwise treat diseased or damaged tissues and organs. Such products can include intact tissue grafts and/or acellular or reconstituted acellular tissues (e.g., acellular tissue matrices from skin, intestine, or other tissues, with or without cell seeding). Such products generally have mechanical properties determined by the tissue source (i.e., tissue type and animal from which it originated) and the processing parameters used to produce the tissue products. Since tissue products are often used for surgical applications and/or tissue replacement or augmentation, the mechanical and biological properties of the tissue products are important. For example, tissue products must be able to provide suitable mechanical support (e.g., to close a tissue defect), while allowing tissue in-growth and regeneration. In some cases, however, it may be desirable to modify the mechanical and/or biological properties of tissue products. Furthermore, in order to improve the performance of tissue products for specific applications, it may be desirable to produce tissue products that have variable mechanical and/or biological properties. Accordingly, the present disclosure provides devices and methods for localized modification of mechanical and/or biological properties of tissue products, including acellular tissue matrices.

SUMMARY

According to various embodiments, a method for treating a tissue matrix is provided. The method can comprise selecting a collagen-containing tissue matrix and cross-linking select portions of the tissue matrix to produce a tissue matrix having mechanical or biological properties that vary across the tissue matrix. In some embodiments, the tissue matrix is an acellular tissue matrix. In certain embodiments, the tissue matrix comprises a dermal tissue matrix. In other embodiments, the tissue matrix is derived from a tissue selected from fascia, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, and intestinal tissue.

In some embodiments, the method comprises cross-linking select portions of the tissue matrix by applying a fluid containing a cross-linking agent to the select portions. In certain embodiments, applying a fluid containing a cross-linking agent to the select portions comprises providing a solid surface having one or more channels configured to allow fluid to flow therethough; contacting the tissue matrix with the surface; and causing fluid containing a cross-linking agent to flow through the channels. In various embodiments, the one or more channels have at least one of a serpentine pattern, a web-like pattern, a circular pattern, a grid pattern, and a linear pattern. In various embodiments, the cross-linking agent comprises at least one of gluteraldehyde, 1-Ethyl-3-[3-dimethylaminopropyl]carbodiimide hydrochloride (EDC), or genepin.

In various embodiments, a method for treating a tissue matrix is provided. The method can comprise selecting a collagen-containing tissue matrix and contacting select portions of the tissue matrix with a proteolytic enzyme to produce a tissue matrix having mechanical properties that vary across the tissue matrix. In some embodiments, the tissue matrix comprises a dermal tissue matrix. In other embodiments, the tissue matrix is derived from a tissue selected from fascia, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, and intestinal tissue.

In some embodiments, contacting select portions of the tissue matrix with a proteolytic enzyme comprises applying a fluid containing the proteolytic enzyme to the select portions. In some embodiments, contacting select portions of the tissue matrix with a proteolytic enzyme comprises providing a solid surface having one or more channels configured to allow fluid to flow therethough; contacting the tissue matrix with the surface; and causing fluid containing the proteolytic enzyme to flow through the channels. In some embodiments, the one or more channels have at least one of a serpentine pattern, a web-like pattern, a circular pattern, a grid pattern and a linear pattern.

In certain embodiments, the enzyme is bromelain. In some embodiments, the enzyme is selected from bromelain, papain, ficin, actinidin, or combinations thereof.

In some embodiments, the method further includes treating the tissue matrix to removal at least some of the cells and cellular components from the tissue matrix. In some embodiments, the method includes removing all the cells and cellular components from the tissue matrix.

In various embodiments, tissue products produced according to any of the disclosed methods are provided.

In certain embodiments, a tissue product is provided. The tissue product can comprise an acellular tissue matrix derived from a collagen-containing tissue, wherein the tissue matrix comprises a flexible sheet, and wherein the tissue matrix comprises select regions of cross-linked or proteolytically digested material, and wherein the mechanical or biological properties of the tissue matrix vary across the flexible sheet.

DESCRIPTION OF THE DRAWINGS

FIG. 5 illustrates an acellular tissue matrix that has been treated to provide localized modification of mechanical properties and/or biological properties, according to certain embodiments.

FIG. 6 illustrates an acellular tissue matrix that has been treated to provide localized modification of mechanical properties and/or biological properties, according to certain embodiments.

DESCRIPTION OF CERTAIN EXEMPLARY EMBODIMENTS

Figure 1A:
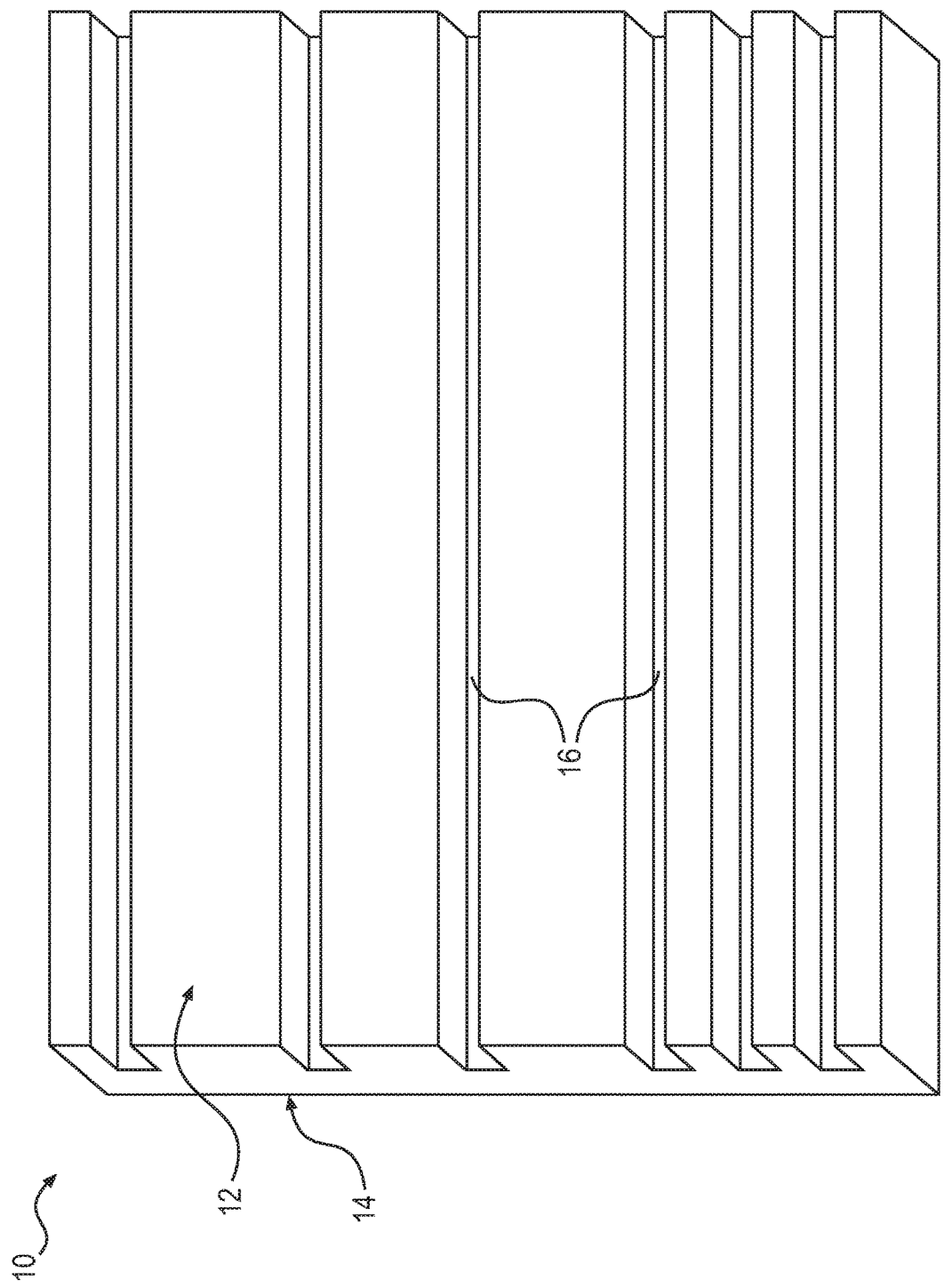
FIGS. 1A-1B illustrate a device for microfluidic modification of a tissue product, according to certain embodiments.

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Any ranges described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

As used herein "tissue product" will refer to any human or animal tissue that contains extracellular matrix proteins. "Tissue products" can include acellular or partially decellularized tissue matrices, as well as decellularized tissue matrices that have been repopulated with exogenous cells.

Various human and animal tissues can be used to produce products for treating patients. For example, various tissue products are available for regeneration, repair, augmentation, reinforcement, and/or treatment of human tissues that have been damaged or lost due to various diseases and/or structural damage (e.g., from trauma, surgery, atrophy, and/or long-term wear and degeneration). Such products can include, for example, acellular tissue matrices, tissue allografts or xenografts, and/or reconstituted tissues (i.e., at least partially decellularized tissues that have been seeded with cells to produce viable materials).

For surgical applications, it is often desirable to produce tissue products that have certain mechanical properties. For example, the tissue product, which may include a sheet of material, should possess sufficient strength to withstand stresses during the intended use. Certain tissue products may be used to repair defects (e.g., hernias), to support surrounding tissues or implants (e.g., for breast augmentation and/or reconstruction), or to replace damaged or lost tissue (e.g., after trauma or surgical resection). Whatever the particular use, the tissue product should have sufficient strength, elasticity, and/or other mechanical properties to function until tissue regeneration and/or repair occurs.

Some tissue products, however, may be functionally improved by altering the mechanical properties of the products. For example, a number of acellular tissue matrix products are available, and often, such tissue matrices are in the form of a flexible sheet of material that has substantially uniform mechanical and/or biological properties over its entire surface area. For some indications, however, it may be desirable to alter the mechanical and/or biological properties of such tissue matrices such that the properties vary across the material. For example, in some embodiments, it may be desirable to strengthen, stiffen, weaken, or make more pliable select regions of a tissue product to produce a product having variable mechanical properties. In addition, in some embodiments, it may be desirable to modify certain elastic or viscoelastic properties of a tissue matrix, including, for example, the resistance to stretching at low deformation levels (e.g., toe-region mechanics).

It may be desirable to treat select regions of the tissue products to control the rate of degradation, cell in-growth, and/or vascularization after implantation. It is known that cross-linking can increase the resistance of tissue matrices to degradation by inflammatory cells within the body, and such increased resistance can slow the rate of weakening after implantation. Accordingly, in some embodiments, it may be desirable to provide localized cross-linking to provide areas of the tissue matrix that maintain their ability to provide mechanical support to an implantation site for longer times after implantation, while simultaneously providing sufficient tissue matrix mass to support normal tissue regeneration within uncross-linked portions of the tissue matrix.

The present disclosure provides methods for treating tissues to provide variable mechanical and/or biological properties along the length, width, or thickness of a tissue matrix. The disclosure also provides tissue products produced using the methods of treatments.

According to various embodiments, a method for treating a tissue matrix is provided. The method can comprise selecting a collagen-containing tissue matrix and cross-linking select portions of the tissue matrix to produce a tissue matrix having mechanical and/or biological properties that vary across the tissue matrix. In some embodiments, the tissue matrix is an acellular tissue matrix. In certain embodiments, the tissue matrix comprises a dermal tissue matrix.

In various embodiments, a method for treating a tissue matrix is provided. The method can comprise selecting a collagen-containing tissue matrix and contacting select portions of the tissue matrix with a proteolytic enzyme to produce a tissue matrix having mechanical properties that vary across the tissue matrix.

The tissue products according to the present disclosure can be selected to provide a variety of different biological and/or mechanical properties. For example, an acellular tissue matrix or other tissue product can be selected to allow tissue in-growth and remodeling to assist in regeneration of tissue normally found at the site where the matrix is implanted. For example, an acellular tissue matrix, when implanted on or into fascia or other soft tissue, may be selected to allow regeneration of the fascia or other soft tissue without excessive fibrosis or scar formation. In certain embodiments, the tissue product can be formed from ALLODERM® or STRATTICE™ (LIFECELL CORPORATION, Branchburg, N.J.), which are human and porcine acellular dermal matrices respectively. Alternatively, other suitable acellular tissue matrices can be used, as described further below. The tissues can be selected from a variety of tissue sources including skin (dermis or whole skin), fascia, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, and intestinal tissue. The methods described herein can be used to process any collagenous tissue type and for any tissue matrix product. For example, a number of biological scaffold materials are described by Badylak et al., and the methods of the present disclosure can be used to treat those or other tissue products known in the art. Badylak et al., "Extracellular Matrix as a Biological Scaffold Material: Structure and Function," Acta Biomaterialia (2008), doi:10.1016/j.actbio.2008.09.013.

In some cases, the tissue matrix can be provided as a decellularized tissue matrix. Suitable acellular tissue matrices are described further below. In other cases, the method can further include processing intact tissue to remove cells or other materials either before, after, or both before and after cross-linking or proteolytic treatment according to the present application. The tissues can be completely or partially decellularized to yield acellular tissue matrices or extracellular tissue materials to be used for patients. For example, various tissues, such as skin, intestine, bone, cartilage, nerve tissue (e.g., nerve fibers or dura), tendons, ligaments, or other tissues can be completely or partially decellularized to produce tissue products useful for patients. In some cases, these decellularized products can be used without addition of exogenous cellular materials (e.g., stem cells). In certain cases, these decellularized products can be seeded with cells from autologous sources or other sources to facilitate treatment. Suitable processes for producing acellular tissue matrices are described below.

In certain embodiments, tissue matrices can be treated to provide localized variation in mechanical and/or biological properties by contacting the tissue matrices with one or more cross-linking agents and/or proteolytic enzymes. Generally, the matrices can be treated by contacting selected portions of the tissue matrices with a fluid containing the agent or enzyme and under conditions (e.g., temperature and/or pH) and for a time sufficient to produce a desired degree of cross-linking and/or proteolysis.

Figure 1B:
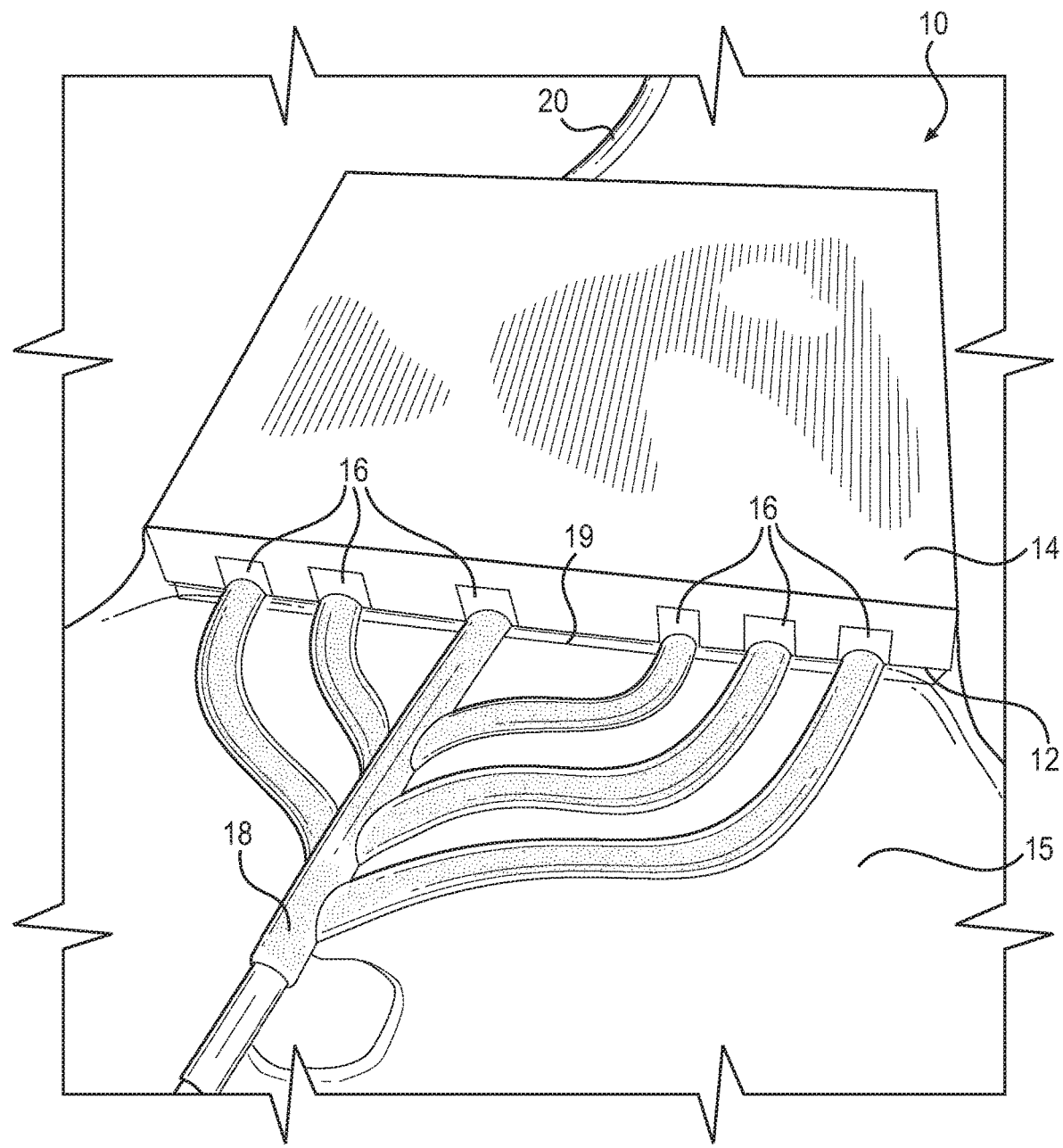

The fluid containing cross-linking agents or enzymes can be applied to selected regions of the tissue matrix in a variety of ways. In certain embodiments, the fluid is made to flow in contact with the tissue matrix to permit contact with only those regions of the tissue matrix that are selected for modification. FIGS. 1A-1B illustrate a device 10 for microfluidic modification of tissue products, according to certain embodiments. As shown in FIG. 1A, the device 10 can include a rigid body with a bottom surface 12 and top surface 14, as well as a number of channels 16. When in use, the device 10 can be placed with the bottom surface 12 and channels 16 facing downward towards a rigid surface 15 (FIG. 1B). A tissue matrix 19 can be placed between the bottom surface 12 and the rigid surface 15 with sufficient pressure to substantially prevent flow of fluid through the tissue matrix 19 other than at regions surrounded by the channels 16. The fluid containing cross-linking agents or enzymes can be made to flow through the channels 16 via entrance and exit fluid supply tubings 18, 20. In some embodiments, each channel 16 can be connected to an individual supply tubing 18, 20, or one or more of the channels can be connected to supply tubing via manifolds, as long as a desired degree of fluid flow is achieved.

The channels 16 can have a variety of shapes, sizes and configurations. In general, the channels 16 should be spaced far enough apart to allow a seal to form between channels when placed in contact with a tissue matrix. Further, suitable channel widths can range from 1 micron to 5 cm, and suitable channel heights can range from 1 micron to 2 mm. In addition, the channel edges should be rounded or blunted to prevent tissue damage.

A number of different cross-linking agents and/or enzymes can be used to treat the tissue matrices. For example, suitable cross-linking agents can include gluturaldyhyde, EDC, genepin, aldehydes, and/or lysyl oxidase; and suitable enzymes can include sulfhydryl proteases such as bromelain. In addition, the enzymes can include bromelain, papain, ficin, actinidin, or combinations thereof. The enzymes and cross-linking agents can be purchased commercially; or enzymes can be extracted from fruit sources. For example, one source of bromelain is MCCORMICK MEAT TENDERIZER, but the enzymes can also be extracted from pineapple and/or purchased in a medical-grade formulation.

The enzymes can be contacted with the tissues to increase the pliability of the tissue without causing undesirable degradation in other mechanical and/or biological properties. For example, when a batch of materials is produced with or without the enzyme treatments discussed herein, the enzyme treatments will not produce an undesirable change in at least one of tensile strength, tear strength, suture strength, creep resistance, collagenase susceptibility, glycosaminoglycan content, lectin content, burst strength, thermal transition temperature, or combinations thereof. In some cases, an undesirable change is a statistically significant reduction any one of tensile strength, tear strength, suture strength, creep resistance, glycosaminoglycan content, lectin content, burst strength; an increase in collagenase susceptibility; or a change (upward or downward) in thermal transition temperature (as measure using differential scanning calorimetry).

In some cases, the enzymes are selected such that they cause site-specific cleavage of proteins within the tissues. For example, it has been found that treatment of porcine dermal materials with bromelain does not cause further alterations in the matrix structure after a certain amount of treatment. Therefore, treatment of dermis with bromelain does not cause further change in the matrix with prolonged exposure or after extended periods of time.

In addition, the enzymes and cross-linking agents can be applied to the tissues in a variety of suitable solutions. For example, bromelain has been found to be effective when applied to tissues in normal saline, but other suitable buffers (e.g., PBS) can be used.

Figure 2:
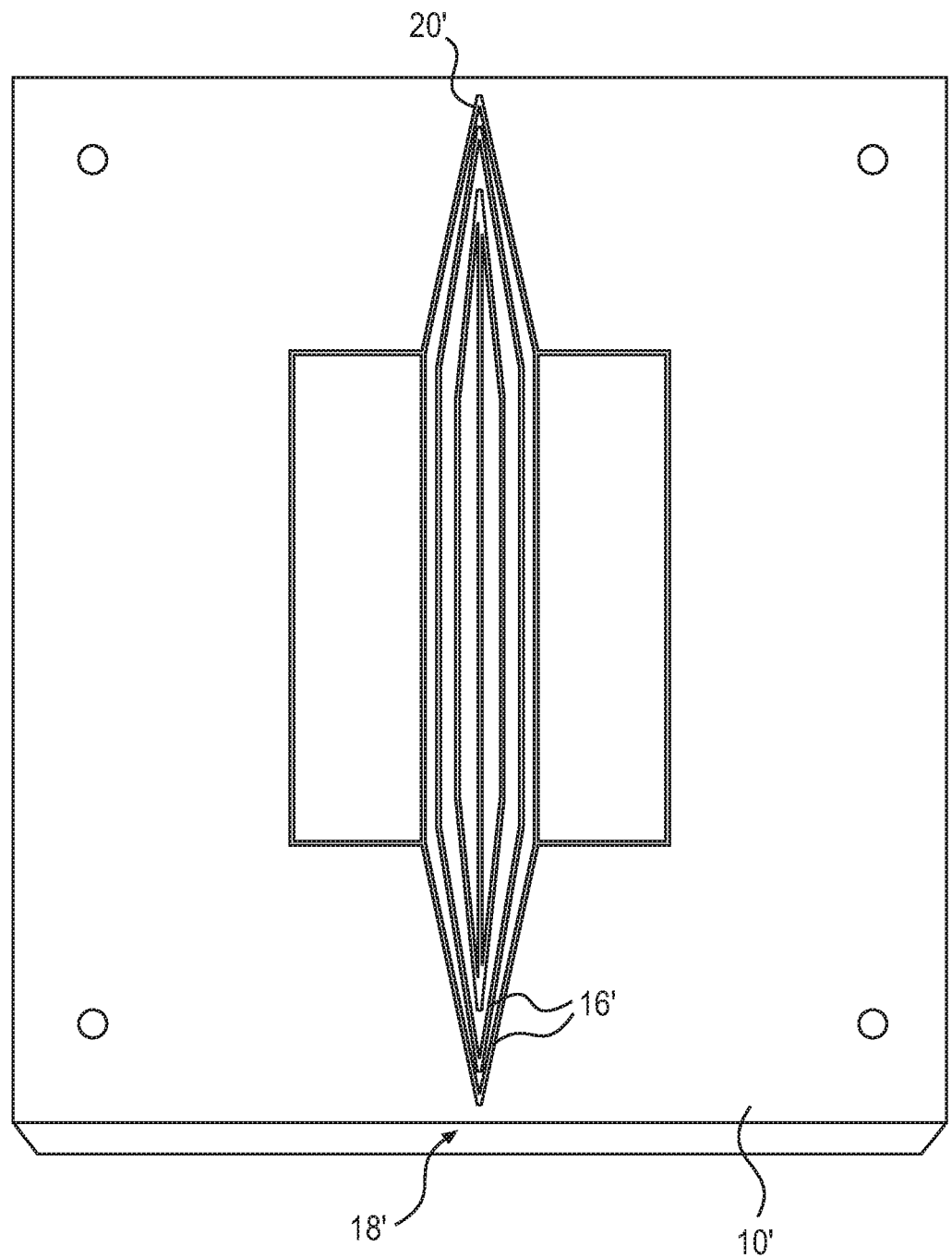
FIG. 2 illustrates a device for microfluidic modification of a tissue product, according to certain embodiments.
Figure 4:
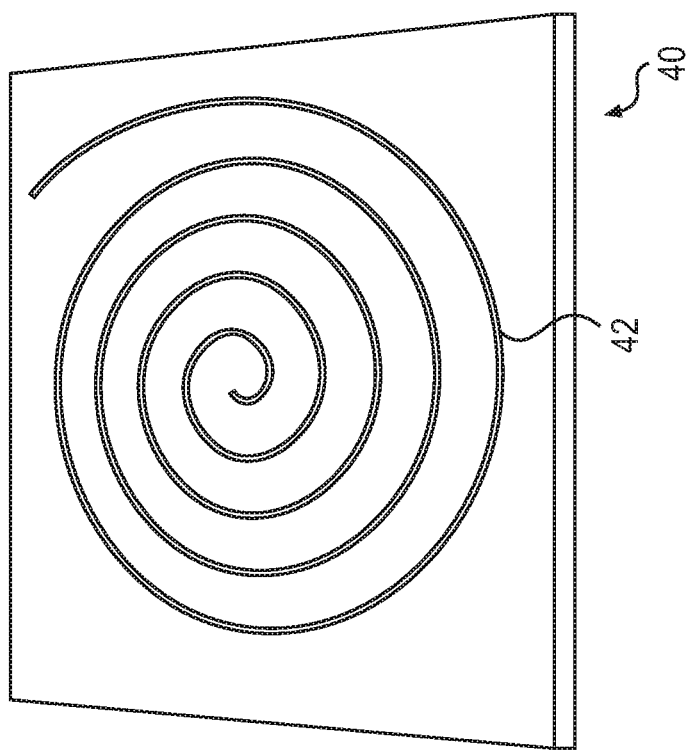
FIG. 4 illustrates an acellular tissue matrix that has been treated to provide localized modification of mechanical properties and/or biological properties, according to certain embodiments.
Figure 3:
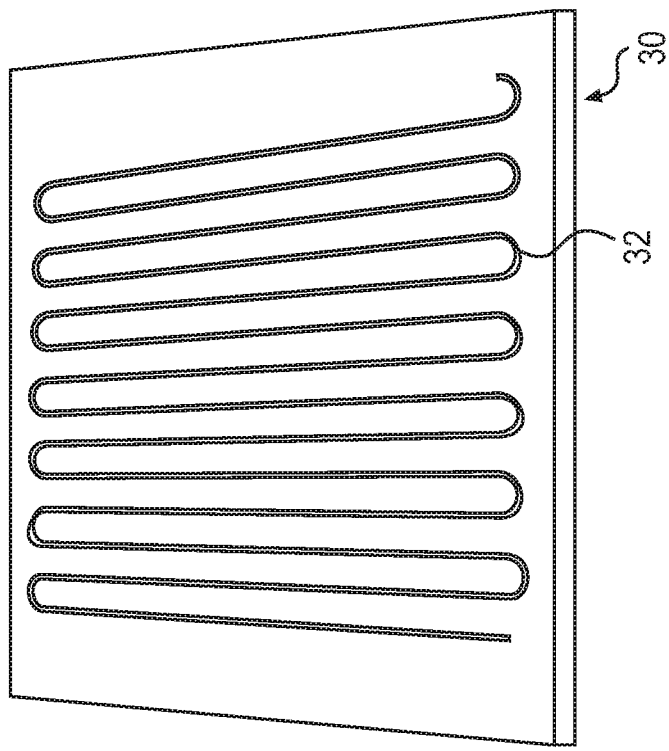
FIG. 3 illustrates an acellular tissue matrix that has been treated to provide localized modification of mechanical and/or biological properties, according to certain embodiments.

The device 10 used to contact the tissue matrix 19 with enzymes and/or cross-linking agents can have a variety of different configurations. For example, as described in further detail below with respect to FIGS. 3-10, the tissue matrix 19 can be treated by cross-linking and/or treatment with proteolytic enzymes at a number of suitable locations to produce a pattern providing desired variations in mechanical and/or biological properties. FIG. 2 illustrates a device 10' for microfluidic modification of tissue products, according to certain embodiments. As shown, the device 10' again includes a rigid structure with channels 16'. In the embodiment of FIG. 2, however, the channels 16' have a shape or pattern that is different than that of FIG. 1, thereby allowing contact of the cross-linking agent or proteolytic enzyme to produce a modified tissue matrix with a different configuration. Furthermore, the device 10' has two openings 18' and 20', which provide passages for flow of fluid into and out of the channels 16', rather than having multiple separate openings 18, 20, as with the device of FIG. 1. Any suitable number of openings may be used to provide adequate flow of fluid through channels 16, 16'.

Figure 11:
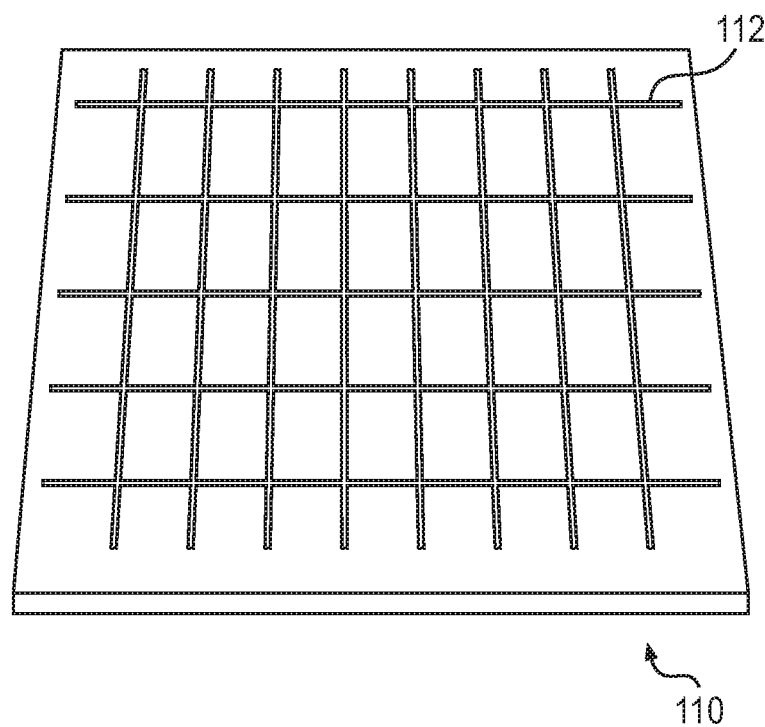
FIG. 11 illustrates an acellular tissue matrix that has been treated to provide localized modification of mechanical properties and/or biological properties, according to certain embodiments.

The methods of the present disclosure can be used to modify mechanical and/or biological properties in a number of different locations. FIGS. 3-10 illustrate acellular tissue matrices that have been treated to provide localized modification of mechanical and/or biological properties, according to certain embodiments. In various embodiments, the tissue matrices can be treated to modify select regions of a sheet-like tissue matrix over regions having a serpentine pattern 32 (FIG. 3), a spiral pattern 42 (FIG. 4), linear patterns 52, 62 (FIGS. 5 and 6), curved patterns 72 (FIG. 7), along linear or longitudinally aligned patterns 82 in a cylindrically wrapped sheet 80 (FIG. 8), in a circular pattern 92 (FIG. 9), in a web-like pattern 102 (FIG. 10), or in a grid pattern 110 (FIG. 11).

The specific pattern of the region selected for localized cross-linking or proteolytic treatment can be selected for a variety of reasons. It is known that cross-linking can increase the resistance of tissue matrices to degradation by inflammatory cells within the body, and such increased resistance can slow the rate of weakening after implantation. Excessive cross-linking, however, can have adverse effects on cell infiltration and regeneration of normal tissue within the tissue matrix. Accordingly, in some embodiments, it may be desirable to provide localized cross-linking to provide areas of the tissue matrix that maintain their ability to provide mechanical support to an implantation site for longer times after implantation, while simultaneously providing sufficient tissue matrix mass to support normal tissue regeneration within uncross-linked portions of the tissue matrix.

Localized protease treatment may be used for a variety of reasons. For example, localized protease treatment can allow production of differing strength or other mechanical properties treating the tissue to make native stronger. In addition, production of tissue matrices with localized pliability may be to allow a surgeon to place tissue in small openings, including passing a tissue matrix through a laparoscopic incision or trocar. In addition, production of tissue with localized pliability can be beneficial to allow matching of compliances with natural tissues or to match anisotropic mechanical properties of tissues.

Figure 8:
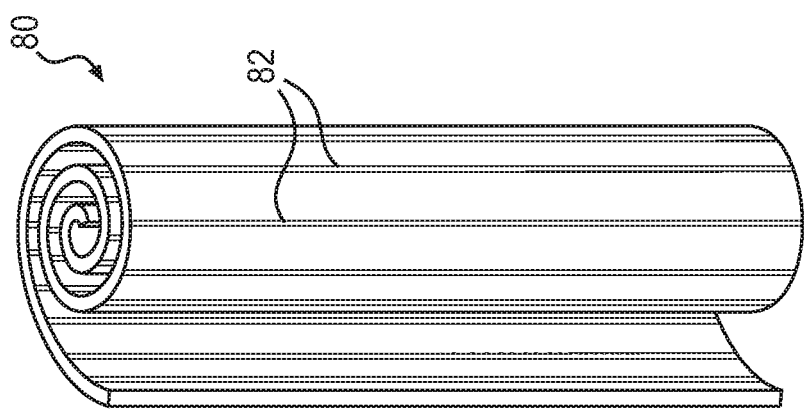
FIG. 8 illustrates an acellular tissue matrix that has been treated to provide localized modification of mechanical properties and/or biological properties, according to certain embodiments.
Figure 7:
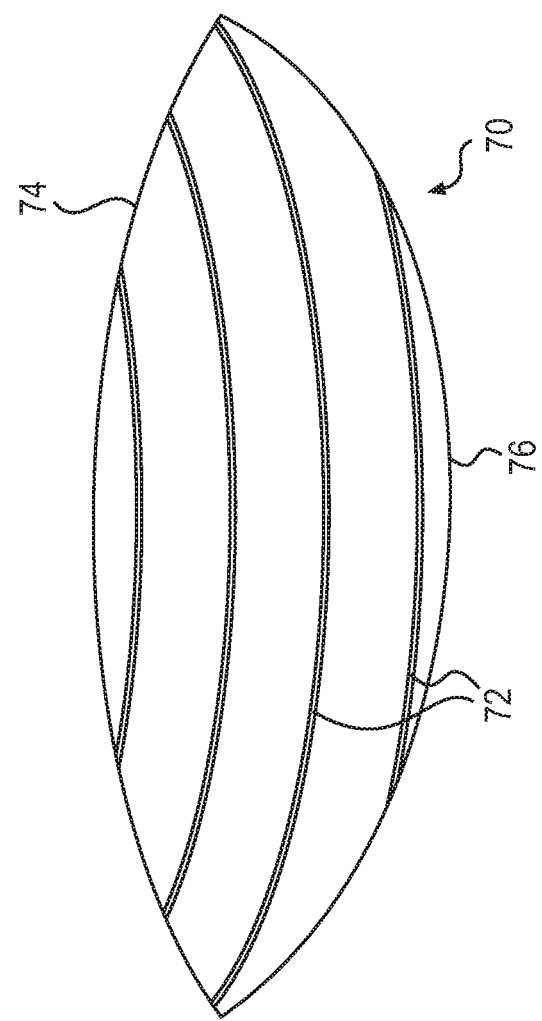
FIG. 7 illustrates an acellular tissue matrix that has been treated to provide localized modification of mechanical properties and/or biological properties, according to certain embodiments.
Figure 10:
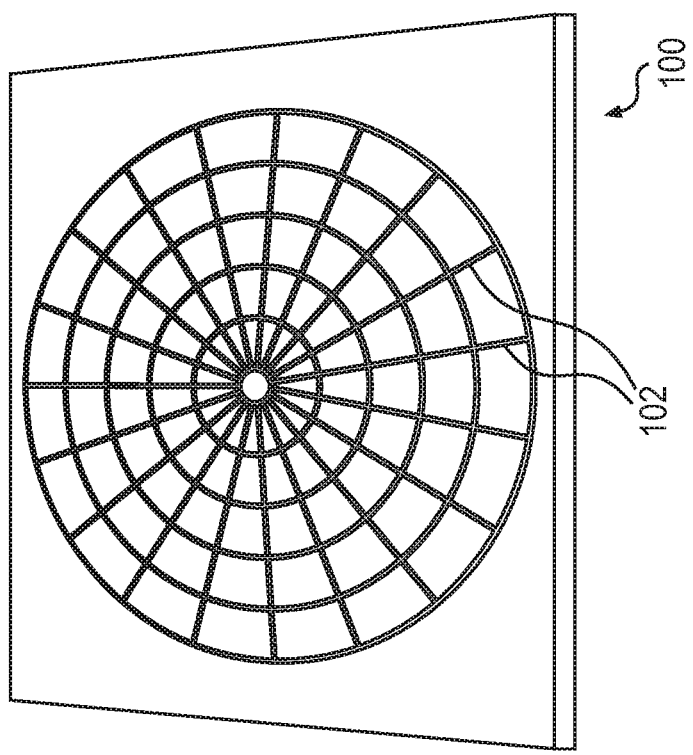
FIG. 10 illustrates an acellular tissue matrix that has been treated to provide localized modification of mechanical properties and/or biological properties, according to certain embodiments.
Figure 9:
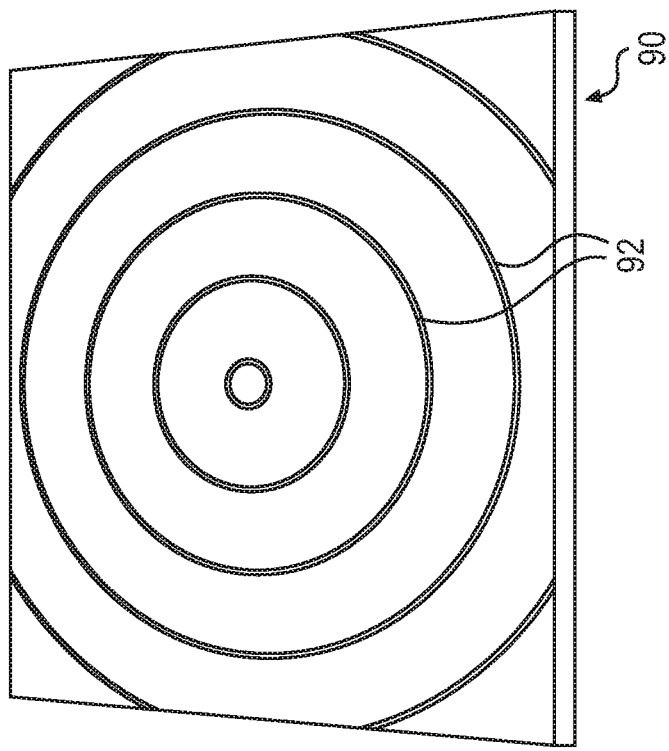
FIG. 9 illustrates an acellular tissue matrix that has been treated to provide localized modification of mechanical properties and/or biological properties, according to certain embodiments.

The specific pattern of localized treatment may be selected based on a desired implantation site or treatment method. For example, in various embodiments, the pattern may be selected to provide a treated tissue matrix having improved mechanical properties (e.g., higher yield strength) along dimensions that may be more likely to experience higher loads during use. For example, in the embodiments of FIGS. 3-6 and 9-10, the pattern may be selected to increase the strength of the sheet of tissue matrix along one or more axes parallel to the sheet of tissue matrix. Similarly, FIG. 7 illustrates a sheet of tissue matrix 70 that can include an upper convex surface 74 and lower convex surface 76, which may be well-suited for use in supporting a breast implant after breast reconstruction or augmentation, and the matrix 70 can be treated along lines 72 selected to increase the strength or elastic modulus of the matrix in direction that may be most likely to fail during use. Similarly, FIG. 8 illustrates a cylindrically shaped matrix 80 having a treatment pattern 82 along lines parallel to an axis of the matrix 80. The cylindrically shaped matrix 80 may be used as a connective tissue replacement (e.g., for a ligament, tendon, or linea alba), and the pattern 82 can be selected to provide desired strength, flexibility, or elastic properties to mimic nature tissue sites and/or to minimize failure rates after implantation.

The concentration, flow-rate, and specific enzyme or chemical used for cross-linking or proteolysis can be selected for a variety of reasons. For example, in general, the specific concentration and flow rate/time of exposure is selected based on the desired degree of cross-linking or proteolysis. In addition, since different enzymes and/or cross-linking agents may have proteolytic or cross-linking effects on different amino acids, combinations of two or more enzymes or cross-linking agents can be used.

Acellular Tissue Matrices

The methods of the present disclosure can be used to provide localized modification of properties of any tissue matrix, including the tissue matrix of cellularized tissues, partially decellularized tissue, or artificially manufactured matrices. In some embodiments, however, the tissue matrices include acellular tissue matrice. The term "acellular tissue matrix," as used herein, refers generally to any tissue matrix that is substantially free of cells and/or cellular components.

Tissue matrices can be processed in a variety of ways, as described below to produce decellularized or partially decellularized tissues. The processing steps described below can be used along with and of (either before or after) the processes described herein for producing tissue matrices having variations mechanical and/or biological properties.

In general, the steps involved in the production of an acellular tissue matrix include harvesting the tissue from a donor (e.g., a human cadaver or animal source) and cell removal under conditions that preserve biological and structural function. In certain embodiments, the process includes chemical treatment to stabilize the tissue and avoid biochemical and structural degradation together with or before cell removal. In various embodiments, the stabilizing solution arrests and prevents osmotic, hypoxic, autolytic, and proteolytic degradation, protects against microbial contamination, and reduces mechanical damage that can occur with tissues that contain, for example, smooth muscle components (e.g., blood vessels). The stabilizing solution may contain an appropriate buffer, one or more antioxidants, one or more oncotic agents, one or more antibiotics, one or more protease inhibitors, and/or one or more smooth muscle relaxants.

The tissue is then placed in a decellularization solution to remove viable cells (e.g., epithelial cells, endothelial cells, smooth muscle cells, and fibroblasts) from the structural matrix without damaging the biological and structural integrity of the collagen matrix. The decellularization solution may contain an appropriate buffer, salt, an antibiotic, one or more detergents (e.g., TRITON X-100™, sodium deoxycholate, polyoxyethylene (20) sorbitan mono-oleate), one or more agents to prevent cross-linking, one or more protease inhibitors, and/or one or more enzymes. In some embodiments, the decellularization solution comprises 1% TRITON X-100™ in RPMI media with Gentamicin and 25 mM EDTA (ethylenediaminetetraacetic acid). In some embodiments, the tissue is incubated in the decellularization solution overnight at 37° C. with gentle shaking at 90 rpm. In certain embodiments, additional detergents may be used to remove fat from the tissue sample. For example, in some embodiments, 2% sodium deoxycholate is added to the decellularization solution.

Skin, parts of skin (e.g., dermis), and other tissues such as blood vessels, heart valves, fascia, cartilage, bone, and nerve connective tissue may be used to create acellular matrices within the scope of the present disclosure. Acellular tissue matrices can be tested or evaluated to determine if they are substantially free of cell and/or cellular components in a number of ways. For example, processed tissues can be inspected with light microscopy to determine if cells (live or dead) and/or cellular components remain. In addition, certain assays can be used to identify the presence of cells or cellular components. For example, DNA or other nucleic acid assays can be used to quantify remaining nuclear materials within the tissue matrices. Generally, the absence of remaining DNA or other nucleic acids will be indicative of complete decellularization (i.e., removal of cells and/or cellular components). Finally, other assays that identify cell-specific components (e.g., surface antigens) can be used to determine if the tissue matrices are acellular. Skin, parts of skin (e.g., dermis), and other tissues such as blood vessels, heart valves, fascia, cartilage, bone, and nerve connective tissue may be used to create acellular matrices within the scope of the present disclosure.

After the decellularization process, the tissue sample is washed thoroughly with saline. In some exemplary embodiments, e.g., when xenogenic material is used, the decellularized tissue is then treated overnight at room temperature with a deoxyribonuclease (DNase) solution. In some embodiments, the tissue sample is treated with a DNase solution prepared in DNase buffer (20 mM HEPES (4-(2-hydroxyethyl)-1-piperazineethanesulfonic acid), 20 mM $CaCl_2$ and 20 mM $MgCl_2$). Optionally, an antibiotic solution (e.g., Gentamicin) may be added to the DNase solution. Any suitable buffer can be used as long as the buffer provides suitable DNase activity.

While an acellular tissue matrix may be made from one or more individuals of the same species as the recipient of the acellular tissue matrix graft, this is not necessarily the case. Thus, for example, an acellular tissue matrix may be made from porcine tissue and implanted in a human patient. Species that can serve as recipients of acellular tissue matrix and donors of tissues or organs for the production of the acellular tissue matrix include, without limitation, mammals, such as humans, nonhuman primates (e.g., monkeys, baboons, or chimpanzees), pigs, cows, horses, goats, sheep, dogs, cats, rabbits, guinea pigs, gerbils, hamsters, rats, or mice.

Elimination of the α-gal epitopes from the collagen-containing material may diminish the immune response against the collagen-containing material. The α-gal epitope is expressed in non-primate mammals and in New World monkeys (monkeys of South America) as well as on macromolecules such as proteoglycans of the extracellular components. U. Galili et al., J. Biol. Chem. 263: 17755 (1988). This epitope is absent in Old World primates (monkeys of Asia and Africa and apes) and humans, however. Id. Anti-gal antibodies are produced in humans and primates as a result of an immune response to α-gal epitope carbohydrate structures on gastrointestinal bacteria. U. Galili et al., Infect. Immun. 56: 1730 (1988); R. M. Hamadeh et al., J. Clin. Invest. 89: 1223 (1992).

Since non-primate mammals (e.g., pigs) produce α-gal epitopes, xenotransplantation of collagen-containing material from these mammals into primates often results in rejection because of primate anti-Gal binding to these epitopes on the collagen-containing material. The binding results in the destruction of the collagen-containing material by complement fixation and by antibody dependent cell cytotoxicity. U. Galili et al., Immunology Today 14: 480 (1993); M. Sandrin et al., Proc. Natl. Acad. Sci. USA 90: 11391 (1993); H. Good et al., Transplant. Proc. 24: 559 (1992); B. H. Collins et al., J. Immunol. 154: 5500 (1995). Furthermore, xenotransplantation results in major activation of the immune system to produce increased amounts of high affinity anti-gal antibodies. Accordingly, in some embodiments, when animals that produce α-gal gal epitopes are used as the tissue source, the substantial elimination of α-gal epitopes from cells and from extracellular components of the collagen-containing material, and the prevention of re-expression of cellular α-gal epitopes can diminish the immune response against the collagen-containing material associated with anti-gal antibody binding to α-gal epitopes.

To remove α-gal epitopes, after washing the tissue thoroughly with saline to remove the DNase solution, the tissue sample may be subjected to one or more enzymatic treatments to remove certain immunogenic antigens, if present in the sample. In some embodiments, the tissue sample may be treated with an α-galactosidase enzyme to eliminate α-gal epitopes if present in the tissue. In some embodiments, the tissue sample is treated with α-galactosidase at a concentration of 300 U/L prepared in 100 mM phosphate buffer at pH 6.0. In other embodiments, the concentration of α-galactosidase is increased to 400 U/L for adequate removal of the α-gal epitopes from the harvested tissue. Any suitable enzyme concentration and buffer can be used as long as sufficient removal of antigens is achieved.

Alternatively, rather than treating the tissue with enzymes, animals that have been genetically modified to lack one or more antigenic epitopes may be selected as the tissue source. For example, animals (e.g., pigs) that have been genetically engineered to lack the terminal α-galactose moiety can be selected as the tissue source. For descriptions of appropriate animals see co-pending U.S. application Ser. No. 10/896, 594 and U.S. Pat. No. 6,166,288, the disclosures of which are incorporated herein by reference in their entirety. In addition, certain exemplary methods of processing tissues to produce acellular matrices with or without reduced amounts of or lacking alpha-1,3-galactose moieties, are described in Xu, Hui. et al., "A Porcine-Derived Acellular Dermal Scaffold that Supports Soft Tissue Regeneration: Removal of Terminal Galactose-α-(1,3)-Galactose and Retention of Matrix Structure," Tissue Engineering, Vol. 15, 1-13 (2009), which is incorporated by reference in its entirety.

After the acellular tissue matrix is formed, histocompatible, viable cells may optionally be seeded in the acellular tissue matrix to produce a graft that may be further remodeled by the host. In some embodiments, histocompatible viable cells may be added to the matrices by standard in vitro cell co-culturing techniques prior to transplantation, or by in vivo repopulation following transplantation. In vivo repopulation can be by the recipient's own cells migrating into the acellular tissue matrix or by infusing or injecting cells obtained from the recipient or histocompatible cells from another donor into the acellular tissue matrix in situ. Various cell types can be used, including embryonic stem cells, adult stem cells (e.g. mesenchymal stem cells), and/or neuronal cells. In various embodiments, the cells can be directly applied to the inner portion of the acellular tissue matrix just before or after implantation. In certain embodiments, the cells can be placed within the acellular tissue matrix to be implanted, and cultured prior to implantation.

What is claimed is:

1. A method for treating a tissue matrix, comprising:
   selecting a collagen-containing tissue matrix; and
   providing a solid surface having one or more channels configured to allow fluid to flow therethrough;
   contacting the tissue matrix with the surface; and
   causing fluid containing a cross-linking agent to flow through the channels and contact select portions of the tissue matrix to produce a tissue matrix having mechanical or biological properties that vary across the tissue matrix.

2. The method of claim 1, wherein the tissue matrix is an acellular tissue matrix.

3. The method of claim 1, wherein the tissue matrix comprises a dermal tissue matrix.

4. The method of claim 1, wherein the tissue matrix is derived from a tissue selected from fascia, pericardial tissue, dura, umbilical cord tissue, placental tissue, cardiac valve tissue, ligament tissue, tendon tissue, arterial tissue, venous tissue, neural connective tissue, urinary bladder tissue, ureter tissue, and intestinal tissue.

5. The method of claim 1, wherein the one or more channels have at least one of a serpentine pattern, a web-like pattern, a circular pattern, a grid pattern, and a linear pattern.

6. The method of claim 1, wherein the cross-linking agent comprises at least one of gluteraldehyde and 1-Ethyl-3-[3-dimethylaminopropyl]carbodiimide hydrochloride (EDC).

7. The method of claim 1, further including treating the tissue matrix to remove at least some of the cells and cellular components from the tissue matrix.

8. The method of claim 7, including removing all the cells and cellular components from the tissue matrix.

9. A method for treating a tissue matrix, comprising:
   selecting a collagen-containing tissue matrix; and
   contacting a select portion of the tissue matrix with a cross-linking agent to produce a tissue matrix having different mechanical properties in the select portion than in a portion of the tissue matrix that was not contacted,
   wherein contacting the select portion of the tissue matrix with a cross-linking agent comprises:
      providing a solid surface having one or more channels configured to allow fluid to flow therethrough;
      contacting the tissue matrix with the surface; and
      causing fluid containing the cross linking agent to flow through the one or more channels.

* * * * *